(12) United States Patent
Patel et al.

(10) Patent No.: US 7,297,789 B2
(45) Date of Patent: Nov. 20, 2007

(54) PROCESS OF PREPARATION OF OLANZAPINE FORM I

(75) Inventors: Hiren V. Patel, Fords, NJ (US); Anup K. Ray, Staten Island, NY (US); Pramod B. Patel, Bordentown, NJ (US); Mahendra R. Patel, East Brunswick, NJ (US)

(73) Assignee: Sandoz, Inc., Princeton, NJ (US)

( * ) Notice: Subject to any disclaimer, the term of this patent is extended or adjusted under 35 U.S.C. 154(b) by 406 days.

(21) Appl. No.: 10/449,643

(22) Filed: May 30, 2003

(65) Prior Publication Data

US 2004/0048854 A1    Mar. 11, 2004

Related U.S. Application Data

(63) Continuation-in-part of application No. 10/160,958, filed on May 31, 2002, now abandoned.

(51) Int. Cl.
*A61K 31/55* (2006.01)
*C07D 487/02* (2006.01)
*A61P 25/18* (2006.01)

(52) U.S. Cl. ........................ 540/557; 514/220
(58) Field of Classification Search .......... 514/220; 540/557
See application file for complete search history.

(56) References Cited

U.S. PATENT DOCUMENTS

| | | | |
|---|---|---|---|
| 3,985,750 A | 10/1976 | Protiva et al. | 260/268 TR |
| 4,115,568 A | 9/1978 | Chakrabarti et al. | 424/250 |
| 4,115,574 A | 9/1978 | Chakrabarti et al. | 424/250 |
| 5,229,382 A | 7/1993 | Chakrabarti et al. | 514/220 |
| 5,605,897 A | 2/1997 | Beasley, Jr. et al. | 514/220 |
| 5,627,178 A | 5/1997 | Chakrabarti et al. | 514/220 |
| 5,631,250 A | 5/1997 | Bunnell et al. | 514/220 |
| 5,637,584 A | 6/1997 | Larsen | 514/220 |
| 5,703,232 A | 12/1997 | Bunnell et al. | 540/557 |
| 5,736,541 A | 4/1998 | Bunnell et al. | 514/220 |
| 5,817,655 A | 10/1998 | Chakrabarti et al. | 514/220 |
| 5,817,656 A | 10/1998 | Beasley, Jr. et al. | 514/220 |
| 5,817,657 A | 10/1998 | Beasley, Jr. et al. | 514/220 |
| 6,008,216 A | 12/1999 | Chakrabarti et al. | 514/220 |
| 6,020,487 A | 2/2000 | Bunnell et al. | 540/557 |
| 6,251,895 B1 | 6/2001 | Larsen et al. | 514/220 |
| 6,348,458 B1 | 2/2002 | Hamied et al. | 514/220 |
| 2002/0086993 A1 | 7/2002 | Davies et al. | 540/495 |
| 2002/0165225 A1 | 11/2002 | Hamied et al. | 514/220 |
| 2005/0239772 A1* | 10/2005 | Piechaczek et al. | 514/220 |

FOREIGN PATENT DOCUMENTS

| | | |
|---|---|---|
| EP | 0 454 436 B1 | 10/1991 |
| EP | 0 733 367 B1 | 9/1996 |
| EP | 0 733 634 A1 | 9/1996 |
| EP | 0 733 635 B1 | 9/1996 |
| EP | 0 831 098 B1 | 3/1998 |
| EP | 0 911 028 | 9/1998 |
| EP | 0 733 634 B1 | 11/2000 |
| EP | 1 095 941 | 5/2001 |
| EP | 1 155 696 A2 | 11/2001 |
| EP | 0 831 097 B1 | 7/2002 |
| WO | WO 96/30374 | 10/1996 |
| WO | WO 02/18390 | 3/2001 |
| WO | WO 01/47933 | 7/2001 |
| WO | WO 02/060906 A2 | 8/2002 |
| WO | WO 03/037903 | 5/2003 |
| WO | WO 03097650 | 5/2003 |
| WO | WO 03/055438 | 7/2003 |

OTHER PUBLICATIONS

Chakrabarti et al., "10-Piperazinyl-4H-thieno[3,2-b][1,5]- and -[3,4-b][1,5]benzodiazepines as Potential Neuroleptics," J. Med. Chem., vol. 23, pp. 884-889 (1980).
Chakrabarti et al., "4-Piperazinyl-10H-thieno[2,3-b][1,5]benzodiazepines as Potential Neuroleptics," J. Med. Chem., vol. 23, pp. 878-884 (1980).
Chakrabarti et al., "Heteroarene-fused Benzodiazepines. Part 1. Synthesis of Thieno-[2,3-b] [1,5]-, -[3,2-b] [1,5]-, and -[3,4-b][1,5]-benzodiazepinones," J. C. S. Perkin I, pp. 937-941 (1978).
Campiani et al., "New Antipsychotic Agents with Serotonin and Dopamine Antagonist Properties Based on a Pyrrolo[2,1-b][1,3]benzothiazepine Structure", *J Med Chem*, vol. 41, No. 20, pp. 3763-3772 (1998).
Mouithys-Mickalad et al., "Electrooxidation Potential as a Tool in the Early Screening for New Safer Clozapine-like Analogues", *J Med Chem*, vol. 44, No. 5, pp. 769-776 (2001).
Piper et al., "10-Propargylaminopterin and Alkyl Homologues of Methotrexate as Inhibitors of Folate Metabolism", *J Med Chem*, vol. 25, pp. 877-880 (1982).
Press et al., "10-(Alkylamino)-4H-thieno[3,4-b][1,5]benzodiazepines. A Novel Class of Potential Neuroleptic Agents", *J Med Chem*, vol. 22, No. 6, pp. 725-731 (1979).

* cited by examiner

*Primary Examiner*—Brenda Coleman
(74) *Attorney, Agent, or Firm*—Joseph T. Majka; Gabriel Lopez

(57) ABSTRACT

A process for the preparation of polymorph Form I of 2-methyl-4-(4-methyl-1-piperazinyl)-10H-thieno[2,3-b][1,5] benzodiazepine, or olanzapine.

18 Claims, 2 Drawing Sheets

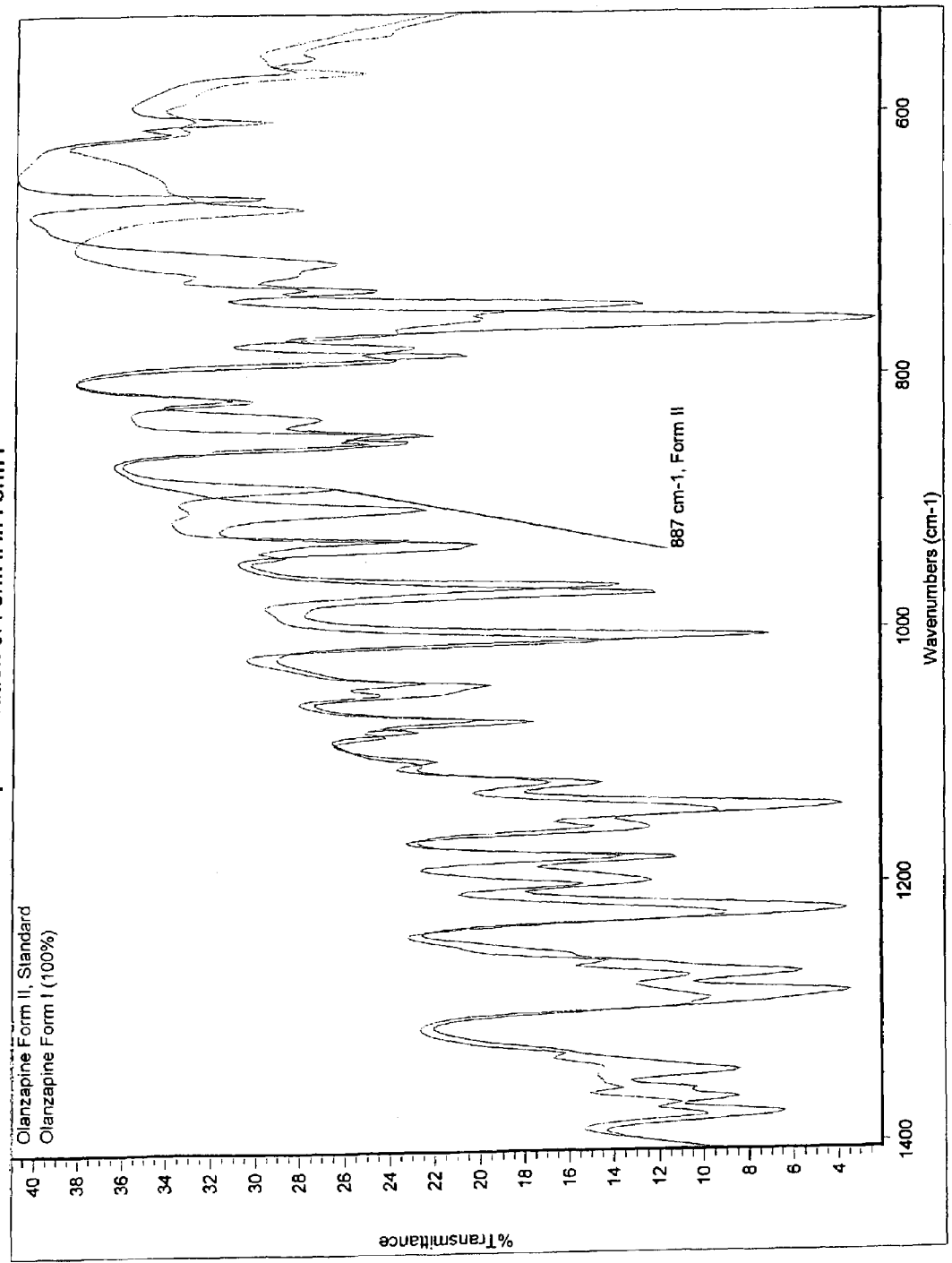
Fig. 1 Expanded spectrum of the region of Olanzapine polymorphic Form I & II showing peak region at 887 cm⁻¹ for quantification of Form II in Form I

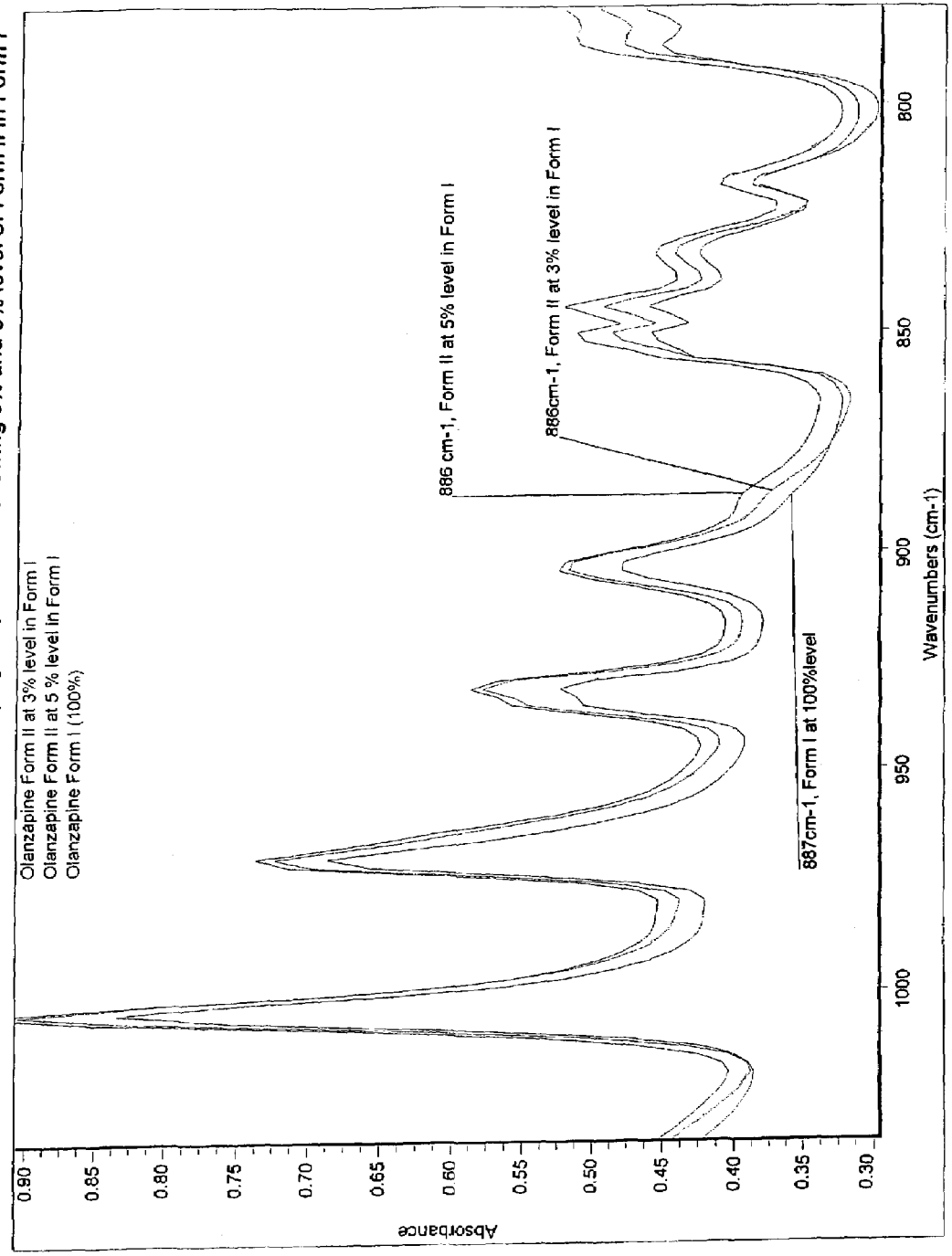

PROCESS OF PREPARATION OF OLANZAPINE FORM I

This application is a continuation-in-part of application Ser. No. 10/160,958, filed May 31, 2002, now abandoned.

BACKGROUND OF THE INVENTION

The compound 2-methyl-4-(4-methyl-1-piperazinyl)-10H-thieno[2,3-b][1,5]benzodiazepine is named olanzapine according to the U.S.A.N. It is known as an anti-psychotic agent. Form I of 2-methyl-4-(4-methyl-1-piperazinyl)-10H-thieno[2,3-b][1,5]benzodiazepine, having m.p. 195° C., is used in pharmaceutical formulations. A process to prepare olanzapine is disclosed in U.S. Pat No. 5,229,382, which is incorporated herein by reference. The last step of the reaction disclosed in the patent comprises mixing 4-amino-2-methyl-10H-thieno[2,3-b][1,5]benzodiazepine and 4-methylpiperazine and refluxing in a suitable organic solvent to yield the desired Form I. It has been found that olanzapine prepared according to the process of the '382 patent is contaminated with olanzapine Form II as an impurity. Accordingly there is a need for a process to prepare olanzapine Form I free of the Form II impurity.

SUMMARY OF THE INVENTION

The present invention provides a process to prepare olanzapine Form I free from impurity with Form II. The present invention provides an improvement to the process of the prior art. This improvement is in the purification and separation of olanzapine Form I from the reaction mixture by the application of a different pH in its solution state with different organic solvents. This technique yields very stable pure anhydrous polymorphic Form I which is free of other polymorphs and solvating agents such as water and organic solvents. Form I olanzapine prepared by the process of the present invention also has satisfactory color and thermal stability for use in a pharmaceutical solid dosage form. The process of the present invention is environmentally friendly and can be applied in large scale, e.g. on the kg level, for commercial manufacturing of olanzapine Form I.

DETAILED DESCRIPTION OF THE DRAWINGS

FIG. 1 is the FT-IR spectrum of olanzapine Form I prepared according to the present invention.

FIG. 2 is the FT-IR spectrum of Form I olanzapine prepared according to the present invention and olanzapine Form II standard.

DETAILED DESCRIPTION OF THE INVENTION

The present invention is directed to a process for producing olanzapine FormI, which comprises reacting N-methylpiperazine and a compound of formula I:

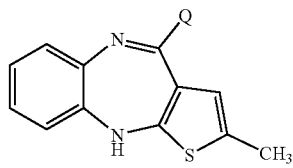

in which Q is a radical capable of being split off.

The radical Q can, for example, be an amino group or a mono- or dialkyl-substituted amino group (each alkyl substituent containing 1 to 4 carbon atoms), hydroxyl, thiol, or an alkoxy, alkylthio, or alkylsulphonyl group containing 1 to 4 carbon atoms, such as methoxy or methylthio, or a halogen, such as chlorine. Preferably, Q is amino (—$NH_2$), hydroxyl, or thiol, amino being preferred. The amidine of formula I, where Q is —$NH_2$, can be in a salt form, for example a salt of a mineral acid such as the hydrochloride.

The reaction is carried out in the presence of an aprotic high boiling solvent, preferably anhydrous dimethyl sulfoxide, at a temperature of 50° C. to 200° C., or 90° C. to 130° C., or from 115° C. to 120° C., or around 110° C. The aprotic solvent, preferably anhydrous, may be dimethyl sulfoxide, dimethylformamide, or mixtures of either of these with toluene. The resulting olanzapine is purified in an acidic medium followed by extraction with organic solvents. The acidic medium for the purification step can be prepared with an organic acid, preferably 40-60% acetic acid. The resulting mixture is then basified (pH 7.5-9.0) under cold conditions, 0° C. to 10° C., preferably to a pH of 7.5-8.5, using an inorganic base such as sodium hydroxide, potassium hydroxide or lithium hydroxide. Sodium hydroxide is the preferred agent. More preferably 30-60% aqueous sodium hydroxide is used. After the desired pH is obtained, the mixture is subject to extraction using a low boiling organic solvent such as diethylether, dichloromethane, dichloroethane, chloroform, ethyl acetate, or other low polar ketonic solvents. Preferably, the solvent is dichloromethane.

After extraction with a low boiling organic solvent, a high boiling basic solvent is then added to the aqueous phase comprising olanzapine. A critical step lies in the use of a basic solvent to purify and separate out olanzapine Form I. "Basic solvent" as used herein refers to the solvent state that results from the combination of an inorganic base and a high boiling solvent. Examples of high boiling solvents include toluene, methyl ethyl ketone, and acetonitrile. Toluene is most preferred. In a preferred embodiment, the basic solvent comprises toluene and alcoholic sodium hydroxide. Examples of alcohols include methanol, ethanol and isopropanol, with methanol being most preferred. The most preferred basic solvent is toluene and methanolic sodium hydroxide.

In one embodiment or the present invention, prior to extraction, the solution is made basic to a pH of about 7.5-9.0 using aqueous sodium hydroxide. With the solution in this basic state, extraction is done with dichloromethane. Each extraction step produces an aqueous phase and a dichioromethane phase. After washings and extraction, the residual dichioromethane is completely removed by rotary evaporation since it can cause conversion to olanzapine Form II. After removal of the dichloromethane, a high boiling solvent, such as toluene, and a basic solvent such as methanolic NaOH are added. To increase yield, pure olanzapine Form I can be crystallized from the basic solvent state by seeding. Crystallization is preferably accomplished at 0° C. to 30° C. The prior art method used toluene as solvent. However, toluene alone also results in some Form II contamination. By the addition of toluene in a basic state only polymorph Form I is obtained.

In another embodiment of the present invention, the reaction mixture is extracted using a low boiling point solvent with good solubility, preferably dichloromethane, prior to basifying, to pH 7.5-9.0, as discussed above.

Another embodiment of the invention is ultra-pure olanzapine Form I, i.e., olanzapine Form I substantially free of other polymorphic forms of olanzapine; in particular, free of olanzapine Form II. By substantially free is meant 98-100%, preferably at least 99%, free of other polymorphic forms.

Another embodiment of the invention is a pharmaceutical composition comprising ultra-pure olanzapine Form I and a pharmaceutically acceptable diluent or carrier therefor.

Another embodiment of the invention is a method of treating a person in need thereof, e.g., someone suffering from or susceptible to psychosis, acute mania, or mild anxiety states, which comprises administering to said person an effective amount of ultra-pure olanzapine Form I.

The invention will now be illustrated by the following examples, which are illustrative and not intended to limit the scope of the invention.

EXAMPLE 1

Ultra-Pure Olanzapine Form I

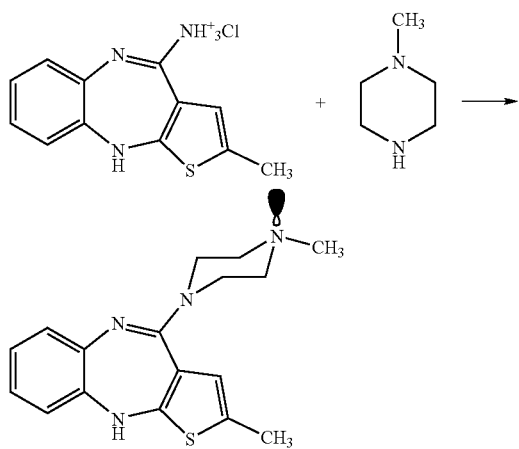

A three necked flask, fitted with a nitrogen gas inlet and a water condenser with calcium chloride guard tube, is charged with 4-amino-2-methyl-10H-theino[2,3-b][1,5]benzodiazepine HCl (5.0 g, 0.0188 mol), 1-methylpiperazine (13.0 mL, 0.11 mol, 99.0%, Aldrich Chemicals, USA) and anhydrous dimethyl sulfoxide (30.0 mL, Aldrich Chemicals, USA, water<0.1%). The reaction mixture is stirred at 112-115° C. (oil bath temperature 115° C.) for 16 hours under continuous flow of nitrogen to drive away the ammonia gas generated during the reaction. The reaction is monitored by HPLC and it is found that within 16 hours 97% product is formed. The reaction mixture is cooled to room temperature (24-25° C.) and added dropwise to a mixture of dichloromethane:water:methanol (190:190:15), (395 mL). After addition, the reaction mixture is stirred for 30 minutes at room temperature. The resulting mixture is yellowish hazy with a dark brown organic layer settled at the bottom of the flask. The dark brown colored dichloromethane layer is separated from the aqueous hazy phase.

After separating the organic layer, the aqueous hazy phase is again extracted with dichloromethane (1×100.0 mL). The combined dichloromethane phases (total volume 290.0 mL) are extracted twice with 50% aqueous acetic acid solution (1×100 mL, 1×75.0 mL). A dark orange color acetic acid layer is separated. The pH of the acetic acid solution is found to be around 3.0-3.5 when tested by litmus paper. Combined aqueous acetic acid solution is basified, to pH 7.5-8.5, using 40% aqueous sodium hydroxide solution under cold conditions (0-10° C.). After attaining the desired pH of the solution, 200 mL dichloromethane is added and stirred. The content is transferred to a separating funnel and is vigorously shaken. The dichloromethane layer is separated and the aqueous phase is again extracted with dichloromethane (1×75.0 mL). The combined dichloromethane extracts are washed with cold saturated sodium chloride solution (1×30.0 mL) and dried over anhydrous sodium sulfate. Removal of solvent on a rotary evaporator with a water bath temperature of 45° C., gives a dark orange brown viscous liquid. To this viscous liquid, 80-85.0 mL dry toluene is added.

The toluene containing crude olanzapine is transferred into a dry 250 mL single necked round bottom flask. Methanolic sodium hydroxide solution (0.32 g sodium hydroxide dissolved in 3.0-4.0 mL methanol by sonication) is added and the mixture is heated in an oil bath at 60° C. for 2 hours. After the stipulated time, 20-25% of the total volume of solvent is evaporated on a rotary evaporator, with a 55-60° C. water bath, to ensure the complete removal of dichloromethane and trace amounts of water, resulting in a final volume of between 55-60 mL. The hot solution is removed from the water bath and cooled in an ice bath with stirring. Within 2-3 minutes, the solution is quickly seeded with previously prepared ultra pure olanzapine Form I, as determined by X-Ray and IR, with stirring. Stirring is continued for 40-45 minutes. The yellowish solid obtained in the solution is filtered off, washed with 1.5-2.0 mL dichloromethane and dried on a vacuum pump for 50-60 minutes to give 4.85 g (82.4% yield) of olanzapine Form I. The solid obtained is crushed to a fine powder and air dried to remove traces of dichloromethane. Karl Fisher analysis indicates 5000-8000 ppm water content. The material is dried in an oven at 65° C. for 1.5-2.0 hours and analyzed for water (670-860 ppm water). The weight of the title product is 4.80 g (82% yield), HPLC purity=99.83%, polymorphic purity is 100% as no detectable polymorph II is observed by X-ray and IR, as shown in Example 3.

The HPLC conditions are as follows: Column: SymmetryC$_{18}$, 4.6×250 mm $\lambda_{max}$: 254 nm Flowrate: 1.0 mL/min.

Run Time: 70 minutes

The buffer comprises 5.4 g potassium phosphate; 0.5 g heptanesulfonic acid sodium salt and 0.5 g 1-octanesulfonic acid sodium salt dissolved in 500 mL DI water and adjusted the pH to 2.6 using conc. phosphoric acid. The mobile phase was 500 mL buffer/300 mL acetonitrile/200 mL methanol. The final pH of the mobile phase is about 3.6. The concentration of the standard is 100 μg/mL; the injection volume is 15 μl; and RT=4.6-4.7 min.

EXAMPLE 2

Recrystallization

From the dried yellowish solid prepared according to Example 1, 2.0 g (0.0064 mol) is transferred into a single necked round bottom flask provided with a magnetic stirrer. To the solid, 40.0 mL dry toluene and methanolic sodium hydroxide solution (0.052 g sodium hydroxide pellets dissolved in 2.0 mL methanol by sonication) are added. To this mixture 3.5-4.0 mL dichloromethane is added.

The mixture is heated for 5-10 minutes in an oil-bath at 60-65° C. until a clear solution is obtained. After heating, the solution is transferred into an ice bath and seeded with previously prepared ultra-pure olanzapine Form I. The solution is stirred for 30-35 minutes at 0-10° C. The yellowish solid obtained is filtered on vacuum pump and washed with 2.0-2.5 mL dichloromethane. The solid is dried on a vacuum pump for 40-45 minutes. The solid obtained is crushed into a fine powder and air dried to remove traces of dichloromethane. The air dried material is further dried in the oven at 65° C. for 1.5-2.0 hours and analyzed for water content. Karl Fisher study shows 670-860 ppm water content. The weight of olanzapine FormI is 1.93 g (95.0% crystallization yield) of 99.96% HPLC purity.

EXAMPLE 3

X-Ray Powder Diffractometry Study

Olanzapine Form I prepared according to Example 1 is analyzed by X-ray, IR, and DSC and found to conform to a commercially available reference standard olanzapine Form I. DSC of the olanzapine Form I prepared according to the present invention shows an endotherm peak at 195° C.

The X-ray powder diffractometry (XRD) study of olanzapine Form I and Form II is done in the following manner. The polymorph powder is filled into an aluminum holder and exposed to CuKα radiation (40 kV×30 mA) in a wide range X-ray powder diffractometer (Model D5005, Siemens). The instrument is operated in the step-scan mode, in increments of 0.02° 2θ. The angular range is 5 to 50° 2θ and counts are accumulated for 1 second at each step. A typical x-ray diffraction pattern for Form I is as follows, wherein d represents the interplanar spacing and $I/I_0$ represents the typical relative intensities. In the following tables (olanzapine Form I and Form II) only those peaks are listed whose relative intensity $I/I_0$ is equal or greater than 10%.

| FORM I | |
|---|---|
| d | I/Io |
| 9.9463 | 100.00 |
| 8.5579 | 15.18 |
| 6.8862 | 14.73 |
| 4.8333 | 68.37 |
| 4.7255 | 21.88 |
| 4.533 | 17.83 |
| 4.2346 | 18.88 |
| 4.855 | 17.29 |
| 3.7489 | 10.64 |
| 3.6983 | 14.65 |

A typical example of an X-ray diffraction pattern for Form II is as follows, wherein d represents the interplanar spacing and $I/I_0$ (>10%) represents the typical relative intensities. Standard polymorph Form II was obtained from Neuland Laboratories, India.

| FORM II | |
|---|---|
| d | I/Io |
| 10.2689 | 100.00 |
| 4.4787 | 14.72 |
| 4.2294 | 23.19 |
| 4.141 | 11.28 |
| 3.7206 | 14.04 |

EXAMPLE 4

Form I vs Form II

Identification and plymorphic purity of olanzapine Form I prepared according to Example 1 has been investigated by FT-IR. FT-IR can distinguish clearly the presence of either polymorphic Form I or polymorphic Form II in the mixture. A peak-to-peak comparison of the FT-IR for both forms clearly show characteristic regions where one of the forms does not show any peak while the other form does (Table 1).

The expanded FT-IR spectrum (FIG. 1, Table 1 in bold) shows that Form II's peak region at 886 cm$^{-1}$ is missing in Form I and is well separated from the closest peak of Form I at 903 cm$^{-1}$. In a standard addition method using FT-IR, a contamination level of a minimum 2% of Form II in Form I can be detected and quantified. The expanded FT-IR spectrum (FIG. 2) shows Form II at a 3% level and a 5% level in Form I. Reference standard polymorph form I was obtained from Dr. Reddy's Laboratories and Form II from Neuland Laboratories, India.

TABLE 1

| FT-IR of Olanzapine Polymorphic Form I and Form II | |
|---|---|
| Form I (ν, cm$^{-1}$) | Form II (ν, cm$^{-1}$) |
| 661 | — |
| — | 671 |
| — | 746 |
| 758 | — |
| 779, doublet | 785, singlet |
| 832 | — |
| — | 886 |
| 903 | — |
| — | 941 |
| — | 964 |
| 970 | — |
| 1005 | — |
| — | 1009 |
| — | 1102 |
| — | 1259 |
| — | 1330 |
| 1344, singlet | 1344, doublet |
| — | 1369 |
| 1526 | — |

EXAMPLE 5

Synthesis of Olanzapine Polymorphic Form I

A three necked flask, fitted with nitrogen gas inlet and a water condenser with a calcium chloride guard tube, was charged with 4-amino-2-methyl-10H-theino[2,3-b][1,5]benzodiazepine HCl (5.0 g, 0.0188 mol, Neuland Laboratories, India), 1-methylpiperazine (13.0 mL, 0.11 mol, 99.0%, Aldrich Chemicals, USA), and anhydrous dimethyl sulfoxide (30.0 mL, Aldrich Chemicals, USA, water<0.1%). The reaction mixture was stirred at 112-115° C. (oil bath temperature 115° C.) for 16 hours under continuous flow of nitrogen to drive away the ammonia gas generated during the reaction. The reaction was monitored by HPLC and it was found that within 16 hours 97% product was formed. After the reaction, the mixture was cooled to room temperature (24-25° C.) and added dropwise to a mixture of dichloromethane:water:methanol (190:190:15, 395 mL). After addition, the reaction mixture was stirred for 30 minutes at room temperature. The resulting mixture was yellowish hazy with dark brown organic layer settled at the bottom of the flask (500 mL). The dark brown color dichloromethane layer was separated from the aqueous hazy phase. After separating the organic layer, the aqueous hazy phase was again extracted with dichloromethane (1×100.0 mL). The combined dichloromethane phase (290.0 mL) was extracted twice with 50% aqueous acetic acid solution (1×100 mL, 1×75.0 mL). A dark orange color acetic acid layer was separated. The pH of the acetic acid solution was found to be around 3.0-3.5 (tested by litmus paper). The combined aqueous acetic acid solution was basified using 40% aqueous sodium hydroxide solution under cold condition (0-10° C.) to pH 7.5-8.0. (During the basification step, pH above 8.0 results in the appearance of solids.) After attaining the desired pH, dichloromethane was added (200 mL) and the solution was stirred. (In the alternative, the pH may be adjusted after the addition of dichloromethane in the aqueous acetic acid phase). The content was transferred to a separating funnel and vigorously shaken. The dichloromethane layer was separated and the aqueous phase was again extracted with dichloromethane (1×75.0 mL). The combined dichloromethane extract was washed with cold saturated sodium chloride solution (1×30.0 mL) and dried over anhydrous sodium sulfate. While drying, the solution with sodium sulfate is shaken vigorously up and down in order to remove the water efficiently.) Removal of solvent on rotary evaporator (water bath temperature 45° C.) gave a dark orange brown viscous liquid with 10-15% total dichloromethane. To this viscous liquid, 80-85.0 mL dry toluene was added. The toluene containing crude olanzapine was neatly transferred into a dry 250 mL single necked round bottom flask and the mixture was heated (oil bath temperature 60° C.) after the addition of methanolic sodium hydroxide solution (0.32 g sodium hydroxide dissolved in 3.0-4.0 mL methanol by sonication). The reaction mixture was heated for 2 hours at 60° C. After the stipulated time, 20-25% of the total volume of solvent was evaporated on rotary evaporator (water bath temperature 55-60° C.) to ensure the complete removal of dichloromethane and trace amounts of water, resulting in a final volume of the solution between 55-60 mL. The hot solution was removed from the water bath and kept at room temperature. The yellowish solid obtained in the solution was filtered off, washed with a small amount of dichloromethane (1.5-2.0 mL), and dried on a vacuum pump for 50-60 minutes to give 4.85 g (82.4% yield) of the title product. The solid obtained was crushed to a fine powder and air dried to remove all traces of dichloromethane and toluene. Karl Fisher analysis indicated 5000-8000 ppm water content. The material was dried in an oven at 65° C. for 1.5-2.0 hours and analyzed for water (670-860 ppm water). The weight of the title product was 4.80 g (82% yield), HPLC purity=99.83%. X-ray, IR, and DSC conform to the reference standard olanzapine Form I.

EXAMPLE 6

Synthesis of Ultra-Pure Olanzapine Polymorphic Form I

From the dried yellowish solid prepared according to Example 5, 2.0 g (0.0064 mol) was transferred into a single necked round bottom flask provided with a magnetic stirrer. To this 40.0 mL dry toluene and methanolic sodium hydroxide solution (0.052 g sodium hydroxide pellets dissolved in 2.0 mL methanol by sonication) was added. To this mixture 3.5-4.0 mL dichlorolmethane was added. The mixture was heated for 5-10 minutes (oil-bath temperature 60-65° C.) until a clear solution was obtained. After heating, the solution was placed immediately into an ice-bath (ice-bath temperature 0-10° C.) and seeded quickly with previously made pure olanzapine Form I. The solution was stirred for 30-35 minutes at 0-10° C. temperature. The yellowish solid obtained was filtered on a vacuum pump and washed with a small quantity of dichloromethane (2.0-2.5 mL). The solid was dried on a vacuum pump for 40-45 minutes. The obtained solid was crushed into fine powder and air dried to remove all traces of dichloromethane and toluene. The air dried material was dried in the oven at 65° C. for 1.5-2.0 hours and analyzed for water content. Karl Fisher study showed 670-860 ppm water content. The weight of the title product was 1.93 g (95.0% crystallization yield) of 99.96% HPLC purity.

X-ray, IR, DSC of the crystallized product conforms to reference standard olanzapine Form I and equivalent to the results of the solid obtained in first crystallization (as is). FT-IR shows apparently 100% polymorphic purity when compared with 2% standard addition technique of Form II with Form I.

Yield=79%, HPLC Purity=99.86%

X-ray, IR, DSC exactly matches with the product of Example 5.

What is claimed is:
1. A process for preparing polymorphic olanzapine Form I comprising:
   a) reacting 4-amino-2-methyl-10H-thieno[2,3-b][1,5]benzodiazepine HCl and 1-methylpiperazine in an aprotic high boiling solvent or mixtures thereof at a temperature of between about 90° C. to 130° C.;
   b) purifying the product of step a) in an acidic medium;
   c) basifying the product of step b) to a pH of between 7.5-9; and
   d) extracting the product of step c) using a low boiling organic solvent.
2. The process of claim 1 wherein the temperature of step (a) ranges from about 115° C. to about 120° C.
3. The process of claim 1 wherein the temperature of step (a) is about 110° C.
4. The process of claim 1 wherein the aprotic high boiling solvent is selected from the group consisting of dimethyl sulfoxide, dimethylformamide, a mixture of dimethyl sulfoxide and toluene, and a mixture of dimethylformamide and toluene.
5. The process of claim 1 wherein the low boiling organic solvent is selected from the group consisting of diethylether, dichloromethane, dichloroethane, chloroform, ethyl acetate, other low polar ketonic solvents, and mixtures thereof.
6. The process of claim 1 wherein the low boiling organic solvent is dichloromethane.
7. The process of claim 1 wherein the acidic medium is an organic acid.

8. The process of claim 7 wherein the organic acid is acetic acid.

9. The process of claim 1 wherein the product of step b) is basified by adding sodium hydroxide.

10. The process of claim 1 wherein the product of step b) is basified to a pH ranging from about 7.5 to about 8.5.

11. The process of claim 1 wherein the product of step b) is basified to pH ranging from about 7.5 to about 8.

12. The process of claim 1 further comprising crystallization of olanzapine Form I by the steps of
   e) adding a basic solvent; and
   f) seeding the solution of step e) with olanzapine Form I at a temperature ranging from about 0° C. to about 30° C.

13. The process of claim 12 further comprising:
   g) adding toluene in step d), removing the low boiling organic solvent by evaporation, and seeding the toluene solution with pure olanzapine Form I at temperature ranging from about 0° C. to about 30° C., wherein the low boiling organic solvent is selected from the group consisting of diethylether, dichloromethane, dichloroethane, chloroform, ethyl acetate, other low polar ketonic solvents, and mixtures thereof.

14. A process of claim 12 wherein the basic solvent is a combination of an inorganic base and a high boiling solvent.

15. A process of claim 12 wherein the basic solvent is a mixture of toluene and methanolic sodium hydroxide.

16. A process of claim 12 further comprising a crystallization to obtain olanzapine Form I of at least 99.8% HPLC purity.

17. A method for preparing olanzapine Form I comprising mixing 4-amino-2-methyl-10H-thieno [2,3-b][1,5]benzodiazepine hydrochloride with a mixture of 1-methylpiperazine, dimethylsulfoxide, toluene, and methanolic sodium hydroxide.

18. The process of claim 1 further comprising the steps of:
   e) adding a basic solvent to provide a solution; and
   f) crystallizing olanzapine Form I from the solution obtained in step e) at a temperature ranging from about 0° C. to about 30° C.

* * * * *